(12) United States Patent
Bernath et al.

(10) Patent No.: US 9,981,349 B2
(45) Date of Patent: May 29, 2018

(54) TITANIUM WELDING WIRE, ULTRASONICALLY INSPECTABLE WELDS AND PARTS FORMED THEREFROM, AND ASSOCIATED METHODS

(71) Applicant: RTI INTERNATIONAL METALS, INC., Niles, OH (US)

(72) Inventors: Jeffrey J. Bernath, Columbus, OH (US); Sesh A. Tamirisakandala, Solon, OH (US)

(73) Assignee: Arconic Inc., Pittsburgh, PA (US)

( * ) Notice: Subject to any disclaimer, the term of this patent is extended or adjusted under 35 U.S.C. 154(b) by 596 days.

(21) Appl. No.: 14/533,243

(22) Filed: Nov. 5, 2014

(65) Prior Publication Data

US 2015/0056006 A1  Feb. 26, 2015

Related U.S. Application Data

(63) Continuation-in-part of application No. 14/279,451, filed on May 16, 2014, now Pat. No. 9,651,524.

(60) Provisional application No. 61/829,707, filed on May 31, 2013.

(51) Int. Cl.
| | |
|---|---|
| *B23K 35/32* | (2006.01) |
| *C22C 14/00* | (2006.01) |
| *B23K 37/00* | (2006.01) |
| *B23K 1/19* | (2006.01) |
| *G01N 29/04* | (2006.01) |

(52) U.S. Cl.
CPC ............ *B23K 35/325* (2013.01); *B23K 1/19* (2013.01); *B23K 37/00* (2013.01); *C22C 14/00* (2013.01); *G01N 29/043* (2013.01); *G01N 2291/267* (2013.01); *G01N 2291/2694* (2013.01); *Y10T 29/49336* (2015.01); *Y10T 29/49774* (2015.01); *Y10T 403/479* (2015.01)

(58) Field of Classification Search
CPC ...... C22C 14/00; B23K 35/325; B23K 37/00; B23K 1/19
See application file for complete search history.

(56) References Cited

U.S. PATENT DOCUMENTS

| | | | |
|---|---|---|---|
| 4,331,857 A | 5/1982 | Crisci et al. | |
| 4,480,475 A | 11/1984 | Tsao et al. | |
| 4,561,888 A | 12/1985 | Okuda et al. | |
| 4,968,348 A | 11/1990 | Abkowitz | |
| 5,041,262 A | 8/1991 | Gigliotti, Jr. | |
| 5,131,959 A | 7/1992 | Huang | |
| 5,205,876 A * | 4/1993 | Sakai ................. | C22C 14/00 148/421 |
| 5,873,703 A * | 2/1999 | Kelly .................. | B23K 1/0018 228/119 |
| 6,049,060 A * | 4/2000 | Smashey ............ | B23K 9/0026 219/137 R |
| 6,332,935 B1 | 12/2001 | Gorman et al. | |
| 6,370,956 B1 * | 4/2002 | Bewlay ............... | G01N 29/11 73/599 |
| 6,393,916 B1 | 5/2002 | Bewlay et al. | |
| 6,401,537 B1 | 6/2002 | Gigliotti, Jr. et al. | |
| 7,322,396 B2 | 1/2008 | Govern et al. | |
| 8,128,764 B2 | 3/2012 | Miracle et al. | |
| 8,206,121 B2 | 6/2012 | Rose | |
| 2011/0277891 A1 * | 11/2011 | Clemens ............. | C22C 1/02 148/670 |
| 2014/0352148 A1 * | 12/2014 | Tamirisakandala .. | G01N 29/043 29/889.7 |

FOREIGN PATENT DOCUMENTS

| | | |
|---|---|---|
| CN | 102854244 A | 1/2013 |
| CN | 102967693 A | 3/2013 |
| EP | 1887093 | 2/2008 |
| WO | 2005060631 | 7/2005 |
| WO | WO200506031 | 7/2005 |

OTHER PUBLICATIONS

Tamirisakandala, S., R.B. Bhat, J.S. Tiley, and D.B. Miracle. "Grain Refinement of Cast Titanium Alloys Via Trace Boron Addition", Scripta Materialia, 53, 2005, pp. 1421-1426.
Foister, S.A.M.; McKenzie, S.G.; Chivers, R.C., An Experimental Investigation of Ultrasonic "Grain Noise" in Titanium-6AL-4V, Review of Progress in Quantitative Nondestructive Evaluation, vol. 15, 1996, pp. 1479-1485.
Banchet, J.; Sicard, R.; Zellouf, D.E., and Chahbaz, A., Phased Arrays Techniques and Split Spectrum Processing for Inspection of Thick Titanium Casting Components, Review of Quantitative Nondestructive Evaluation, vol. 22, 2003, pp. 793-798.

* cited by examiner

*Primary Examiner* — Jessee Roe
(74) *Attorney, Agent, or Firm* — Greenberg Traurig, LLP

(57) ABSTRACT

A welding wire formed of a trace boron titanium base alloy is provided, along with welds formed from the wire and articles comprising one or more of such welds. A method may include forming such a weld or welds from such a welding wire, and may also include non-destructively inspecting titanium alloy articles comprising one or more of such welds using ultrasonic waves to detect internal flaws.

13 Claims, 6 Drawing Sheets

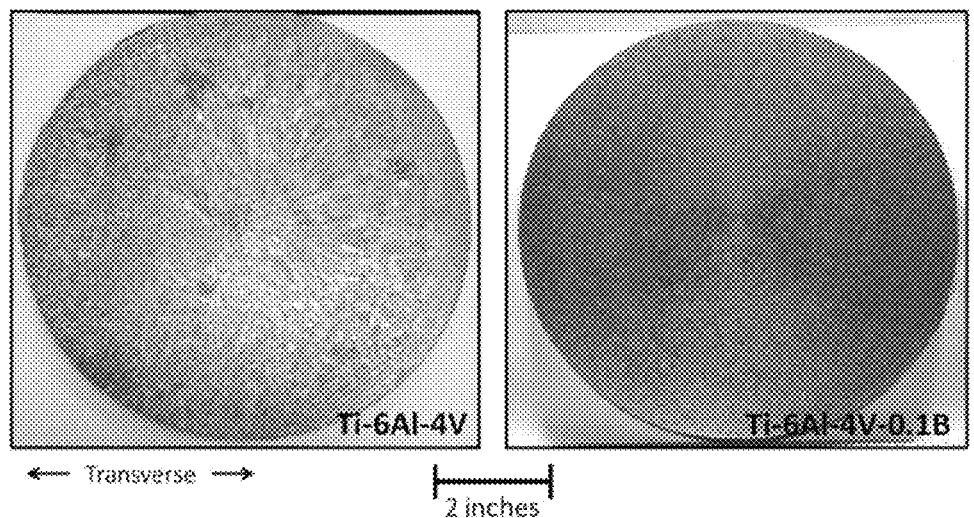
FIG-1A
PRIOR ART
FIG-1C
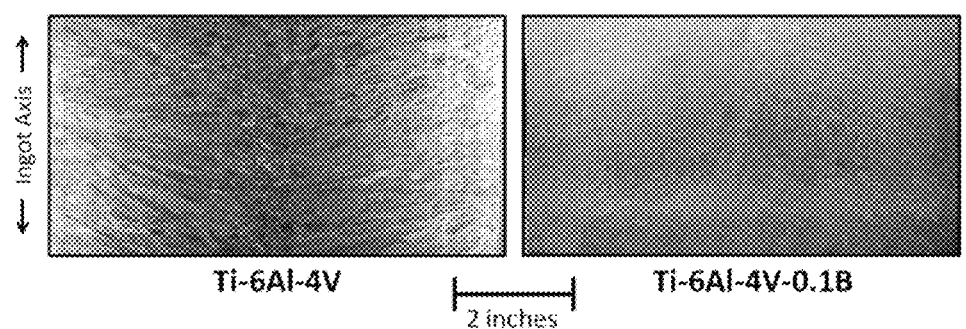
FIG-1B
PRIOR ART
FIG-1D

TITANIUM WELDING WIRE, ULTRASONICALLY INSPECTABLE WELDS AND PARTS FORMED THEREFROM, AND ASSOCIATED METHODS

CROSS REFERENCE TO RELATED APPLICATIONS

This application is a continuation-in-part of U.S. patent application Ser. No. 14/279,451, filed May 16, 2014, which is a non-provisional application of U.S. Provisional Patent Application Ser. No. 61/829,707, filed May 31, 2013, the disclosures of which are incorporated herein by reference.

BACKGROUND OF THE INVENTION

1. Field of the Invention

The present invention may relate to titanium alloy welding wire, titanium alloy articles and methods which may include ultrasonically inspecting such articles, such as articles in the as-cast condition or articles comprising a titanium base alloy weld formed from the welding wire.

2. Description of the Prior Art

The use of titanium alloys for many critical structural applications has resulted in the development and use of a variety of inspection methods. These methods can be classified into volume methods that allow interrogation of the interior (subsurface) of the material and surface methods that permit detection of surface anomalies. These methods are complementary in nature and used concurrently to achieve a high confidence level in detecting undesired conditions that could compromise properties in the material or component. Surface defects are more common, but also are easier to detect and, therefore, catastrophic failure due to surface defects is less likely. Failures from internal defects, on the other hand, are obviously of greater concern compared to surface defects. The ability to consistently find small internal defects has improved the reliability of high performance structures and has led to reductions of unexpected service failures. The structural efficiency of these components also has increased because of the ability to design to higher operating stresses without increasing the risk of unexpected failure.

Ultrasonic inspection of titanium and titanium alloys is the most common inspection method used when the material is intended for use in high performance applications such as the aerospace and energy industries. In this inspection method, ultrasonic waves are induced in the material using a piezoelectric transducer. The transducer is coupled by water or other coupling media to the piece being inspected. The detection of subsurface defects is based on the reflection of some of the incident ultrasonic waves from regions lying along their path. This reflection occurs whenever there is a region that has different acoustic impedance or resistance to the transmission of the ultrasonic waves. During operation, the transducer sends waves, stops sending and waits to detect the reflected waves. There always is a reflection from the front and rear faces of the piece being inspected, which are useful length markers to help physically locate sources of other reflections along the ultrasonic pathway.

Ultrasonic testing typically requires that items to be detected possess high acoustic reflectance behaviors from bulk material under ultrasonic inspection. This different behavior permits the ultrasonic inspection technique to confidently detect subsurface flaws and imperfections. Materials with large, elastically anisotropic grains, such as, but not limited to, cast ingots of steels, titanium alloys and nickel alloys, are often difficult to evaluate by ultrasonic testing. The difficulties arise, at least in part, because sound waves, which are used for ultrasonic inspection, can be partially reflected from grains, and represent a background "noise." The generated background noise can mask flaws in the material, and is thus undesirable. The scattering of sound in a polycrystalline metallic material body, which is also known as attenuation of a propagating sound wave, can be described as a function of at least one of the following: grain dimensions, intrinsic material characteristics, and ultrasound frequency. Use of focused ultrasonic beams to enhance a flaw fraction within any instantaneously insonified volume of material is common. These developed ultrasonic inspection techniques can identify indications based both on maximum signal, as well as signal to noise. However, if the noise level is high, which is the case with coarse grain materials, reliable detection of internal flaws using ultrasonics is not possible.

Titanium ingots in the as-cast condition exhibit extremely coarse grains, in the range of several millimeters to centimeters. These grains follow solidification patterns and are "noisy," which implies that frequent, low amplitude reflections are observed during ultrasonic inspection. In the extreme, this noise gives rise to false positives or insufficient inspection sensitivity necessary to meet the detectability requirements. The most effective solution to this situation is to process the ingots to refine grain structure. Several steps of hot working (repeated heating and mechanical working) to refine grain structures is the standard practice to accomplish this objective. However, this processing is significantly expensive and time consuming. Intermediate products such as billets are routinely inspected ultrasonically to assess whether its quality is suitable for the final processing and eventual service. These intermediate products are products which have already undergone the above-noted hot working before the ultrasonic inspection is performed.

There is a need for an improved approach to be able to reliably inspect titanium billets in the as-cast condition. The improved approach should permit detection of internal flaws with low interference from noise, and also be compatible with subsequent processing of the billets into articles.

Another area which is problematic with respect to ultrasonic inspection relates to titanium base alloy welds and the associated welding process. In most cases, welds are not subsequently hot worked to refine the grain structure as noted above, and thus remain essentially in their original state as part of a final product. Because these welds typically include the coarse grains discussed above, they are not subject to ultrasonic inspection and thus become part of a final product which is either uninspected for internal flaws or which may only be inspected to that effect by more difficult and/or more costly means. Thus, there is a need in the art for titanium alloy welds which can be ultrasonically inspected.

SUMMARY

In one aspect, the invention may provide an apparatus comprising welding wire formed of a titanium base alloy and boron in a range of about 0.05 to 0.20 percent by weight.

In another aspect, the invention may provide an apparatus comprising at least one weld formed of a titanium base alloy and boron in a range of about 0.05 to 0.20 percent by weight.

In another aspect, the invention may provide a method comprising the steps of providing welding wire formed of a titanium base alloy and boron in a range of about 0.05 to 0.20 percent by weight; and forming at least one weld from the welding wire.

BRIEF DESCRIPTION OF THE DRAWINGS

FIGS. 1a-1d include photographs showing a comparison of a sample of a prior art ingot and a sample ingot within the scope of the invention. In particular, FIGS. 1a and 1b are photographs respectively of a transverse section and a longitudinal section of a prior art 8-inch ingot formed of Ti-6Al-4V, illustrating the macro grain structure thereof. FIGS. 1c and 1d are photographs respectively of a transverse section and a longitudinal section of a sample 8-inch ingot formed of Ti-6Al-4V-0.1B.

DETAILED DESCRIPTION OF THE INVENTION

Figure 2:
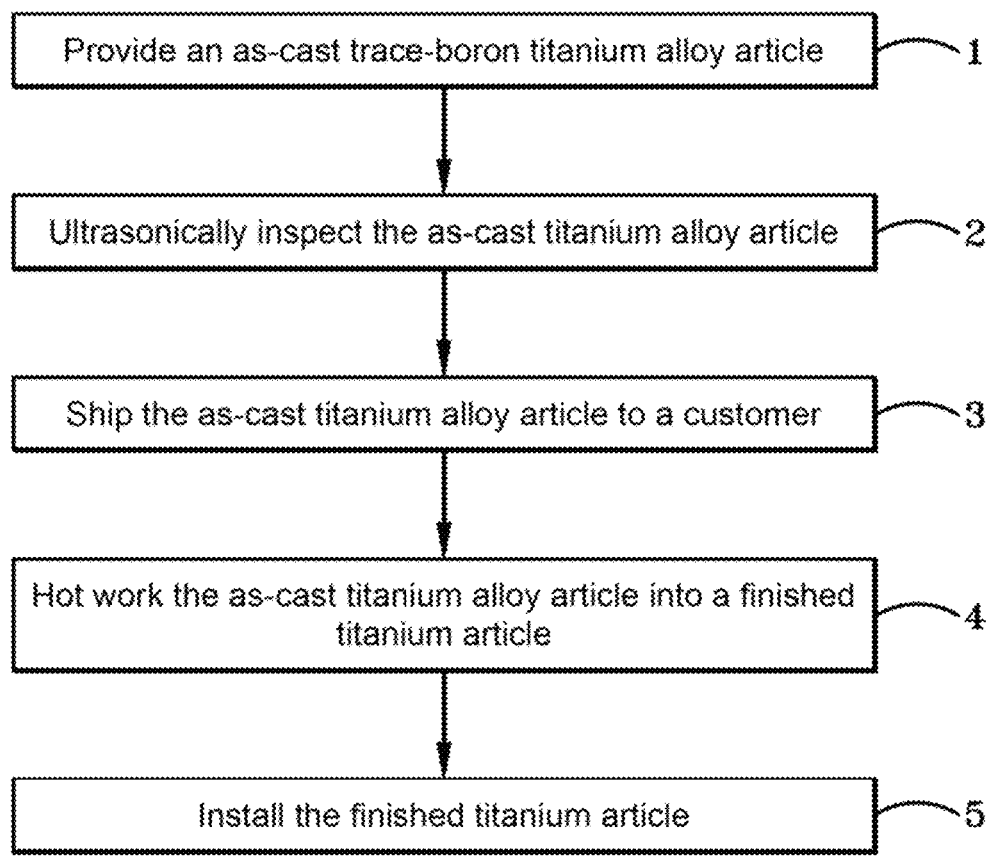
FIG. 2 is a flow chart of a sample method.

One method provided herein allows for the ultrasonic inspectability of titanium alloy articles in the as-cast condition without recourse to significant hot working steps that are typically required. Various titanium alloys may be enhanced with addition of trace boron (B), in a range of about 0.05 or 0.10 to about 0.10, 0.15 or 0.20 percent boron by weight, to refine the grain structure as well as grain orientation in the as-cast condition, both of which minimize the interference with ultrasonic waves, and permit detection of intrinsic flaws with high confidence. The ability to inspect as-cast titanium articles with high confidence, combined with improved hot workability provided by refined grain structure, permits the manufacturing of high-quality titanium alloy articles starting with as-cast billets without the need for significant intermediate processing.

FIG. 1 compares macro grain structures in longitudinal and transverse orientations of 8-inch diameter production ingots of a workhorse titanium alloy, Ti-6Al-4V, melted using plasma arc melting in an inert gas atmosphere in a plasma arc furnace. The as-cast grains in conventional Ti-6Al-4V ingot, as expected, are extremely coarse and follow a macroscopic pattern resulting from the solidification rate. In contrast, the grain structure of Ti-6Al-4V enhanced with trace boron addition exhibits dramatic grain refinement by approximately an order of magnitude and a significantly finer macroscopic grain pattern.

Extremely coarse grains in as-cast Ti-6Al-4V resulted in significant noise levels in ultrasonic inspection (57-59 dB attenuation at 80% amplitude), which prevented any meaningful detection of internal flaws. The as-cast ingot material of Ti-6Al-4V enhanced with trace boron could be successfully ultrasonically inspected using the conventional wrought billet reference standard. An ultrasonic C-scan of the Ti-6Al-4V-0.1B as-cast ingot was performed with an attenuation of 12-16 dB at 80% amplitude, which is an equal or better response than the wrought billet reference standard. The cast ingots of Ti-6Al-4V enhanced with trace boron were also inspected using X-ray technique, and confirmed to be free of voids, thus validating the ultrasonic inspection results.

Coarse columnar grains and colony structures are formed during cooling a conventional titanium alloy from a high temperature as beta Ti transforms to alpha Ti. There is a crystallographic relation between the alpha Ti and the parent beta Ti grain. If there is uniform nucleation of alpha Ti throughout the grain, neighboring alpha Ti particles have different crystallographic orientations, and each behave as distinct acoustic scattering entities. However, if there are only a few sites of alpha Ti nucleation within the beta Ti grain, then the alpha Ti particles in a given area all grow with the same crystallographic orientation, and a colony structure results. This colony becomes the acoustic entity. Since a colony is formed within alpha Ti grain, the colony size will be no larger than the beta Ti grain size. The size of beta Ti grains and the nature of alpha Ti particles in colony structures are important variables that influence ultrasonic noise and ultrasonic inspection in single phase and two-phase titanium alloys and materials. Therefore, the size of beta Ti grains and the nature of alpha Ti particles in colony structures may influence ultrasonic inspection results by creating undesirable noise during ultrasonic inspection. Trace boron addition to conventional titanium alloys produces dramatic refinement of beta Ti grains and also influences orientation of alpha Ti particles, both of which make the material ultrasonically inspectable with low noise levels.

Billets machined from the as-cast ingots that were successfully inspected using ultrasonic inspection could be successfully directly extruded into structural shapes. Tensile properties exhibited by extruded products are presented in Table 1. Properties of extrusions made out of as-cast ingot billets met the minimum property requirements of extrusions made out of conventional wrought billets. Prior art as-cast titanium ingots without the trace boron enhancement, on the other hand, exhibited significant defects and dimensional issues due to poor hot workability. Refined grain structure in trace boron enhanced titanium as-cast ingots imparts good hot workability whereby these as-cast ingots can be used as input stock for making products without recourse to expensive and time consuming hot working steps for refining the grain structure.

TABLE 1

Room temperature tensile properties of extrusions of Ti-6Al-4V with trace boron made directly using as-cast input stock.

| Extrusion Cross-section Shape | Tensile Strength (ksi) | Yield Strength at 0.2% Offset (ksi) | Tensile Elongation in 4D, % | Reduction of Area, % |
| --- | --- | --- | --- | --- |
| TT | 143 | 129 | 17 | 34 |
| TT | 146 | 133 | 19 | 39 |
| ⌐ | 146 | 133 | 17 | 31 |
| AMS 4935 minimum | 130 | 120 | 10 | 20 |

The present invention is applicable to various titanium base alloys, such as, but not limited to, at least one of CP-Ti (Commercial Purity titanium), Ti-64 (Ti-6Al-4V), Ti-17 (Ti-5Al-2Sn-2Zr-4Mo-4Cr), Ti-6242 (Ti-6Al-2Sn-4Zr-2Mo), Ti-6242S (Ti-6Al-2Sn-4Zr-2Mo-0.1Si), Ti-10-2-3 (Ti-10V-2Fe-3Al), Ti-6246 (Ti-6Al-2Sn-4Zr-6Mo), Ti-5-2.5 (Ti-5Al-2.5Sn), Ti-3-2.5 (Ti-3Al-2.5V), Ti-6-4 ELI (Ti-6Al-4V Extra Low Interstitial), Ti-662 (Ti-6Al-6V-2Sn), Beta 21S (Ti-15Mo-2.7Nb-3Al-0.2Si), Beta C (Ti-3Al-8V-6Cr-4Mo-4Zr) and Ti-5553 (Ti-5Al-5V-5Mo-3Cr). The invention is applicable to inspection of as-cast titanium articles using ultrasonic waves to detect defects. The invention enables direct hot working of non-destructively inspected as-cast titanium input materials using processes such as forging, rolling, and extrusion into finished titanium articles.

Referring to the flow chart of FIG. 2, a method of the invention may include providing an as-cast trace-boron titanium alloy article (block 1), ultrasonically inspecting the as-cast titanium alloy article (block 2), shipping the as-cast titanium alloy article to a customer (block 3), hot working the as-cast titanium alloy article into a finished titanium alloy article (block 4) and installing the finished titanium alloy article (block 5).

The step of providing an as-cast trace-boron titanium alloy article typically includes casting the trace-boron titanium alloy article or ingot at a business location to produce the as-cast ingot or article. Although various casting methods may be used, casting the ingot may be achieved in a plasma arc furnace and may include continuous casting of the ingot, which may be cut into pieces or articles of desired length. The ingots may be formed of virtually any titanium alloy with the trace boron in weight percentages discussed above, including the titanium base alloys noted above, to provide, for example, an as-cast trace-boron titanium alloy of one of CP-Ti-0.05-0.20B, Ti-6Al-4V-0.05-0.20B, Ti-5Al-2Sn-2Zr-4Mo-4Cr-0.05-0.20B, Ti-6Al-2Sn-4Zr-2Mo-0.05-0.20B, Ti-6Al-2Sn-4Zr-2Mo-0.1Si-0.05-0.20B, Ti-10V-2Fe-3Al-0.05-0.20B, Ti-6Al-2Sn-4Zr-6Mo-0.05-0.20B, Ti-5Al-2.5Sn-0.05-0.20B, Ti-3Al-2.5V-0.05-0.20B, Ti-6Al-4V-0.05-0.20B Extra Low Interstitial, Ti-6Al-6V-2Sn-0.05-0.20B, Ti-15Mo-2.7Nb-3Al-0.2Si-0.05-0.20B, Ti-3Al-8V-6Cr-4Mo-4Zr-0.05-0.20B and Ti-5Al-5V-5Mo-3Cr-0.05-0.20B. As noted further above, the weight percent of boron in these alloys may be in the range of 0.05 to 0.10, 0.15 or 0.20.

The step of ultrasonically inspecting the as-cast titanium alloy article typically occurs after casting or providing the ingot or article and before any processing such as hot working of the ingot/article. The ingot may be cut to remove portions thereof, but typically no hot working (such as forging, rolling or extrusion) need be performed before the ultrasonic inspection. The ultrasonic inspection typically occurs at the business location and may result in a passed inspection and in a non-destructively inspected as-cast titanium alloy article, which may then be shipped from the business location to a customer remote from the business location. The non-destructively inspected as-cast titanium alloy article may then be subjected to hot working (such as forging, rolling or extrusion) to produce a finished titanium alloy article. The inspected as-cast titanium alloy article need not be shipped prior to hot working, which may be done at the business location as well if desired. Thus, a non-destructively inspected as-cast titanium alloy article may be subjected to hot working at the business location to produce a processed or hot-worked titanium alloy article (which may be a finished titanium alloy article), and for example, then be shipped to a remote location to a customer.

The hot-worked (finished) titanium alloy article may then be installed on or assembled with other components, if necessary, to form a manufactured product which includes the article. For example, the titanium alloy article may be a rotating part in a rotary engine, which may be an aircraft engine, whereby the titanium alloy rotating part is installed on or assembly with other components of the engine to produce the manufactured product in the form of the engine. The article may be configured as an aircraft part, for example, an aircraft engine part such as a nacelle, an engine casing, a rotary compressor blade, a stator airfoil or vane, a combustion chamber, a rotary turbine blade, an exhaust nozzle, an exhaust plug, or an aircraft structural or frame part such as an aircraft pylon part, an aircraft heat shield part or an aircraft fastener. The finished titanium alloy articles may also be used in the energy industry, such as oil drilling components. By way of non-limiting examples, such components may include drill pipe, pipe casing, oil pipes or tubing; offshore piping and sub-sea flowlines; offshore production, export, and re-injection risers and components; oil country tubular goods (OCTG) production tubulars and well casing and liners; offshore deepwater landing strings; offshore well-workover strings; offshore/marine fasteners and structural components; wellhead components; well jewelry or a well jewelry component (packers, safety valves, polished bore receptacles); well logging components and downhole tools; and marine submersible components, such as for remote operated underwater vehicles (ROVs). The finished articles may also include weaponry components for military or other use, such as gun barrels and armor such as used for penetration protection on tanks or other military vehicles.

The method thus allows for the production of a titanium alloy article used in a manufactured product often destined for high performance applications, such as those noted above, without the necessity for the customer or installer of the article having to ultrasonically inspect the article after hot working or other processing subsequent to the original ultrasonic inspection performed on the as-cast ingot or article. The method thus allows for the delivery of an ultrasonically inspected and warranted as-cast trace-boron titanium alloy article to a customer or user which is ready to be processed into a final article, thereby eliminating the need for the customer/user to invest resources and time for ultrasonic inspection equipment and training to operate such equipment.

Figure 3:
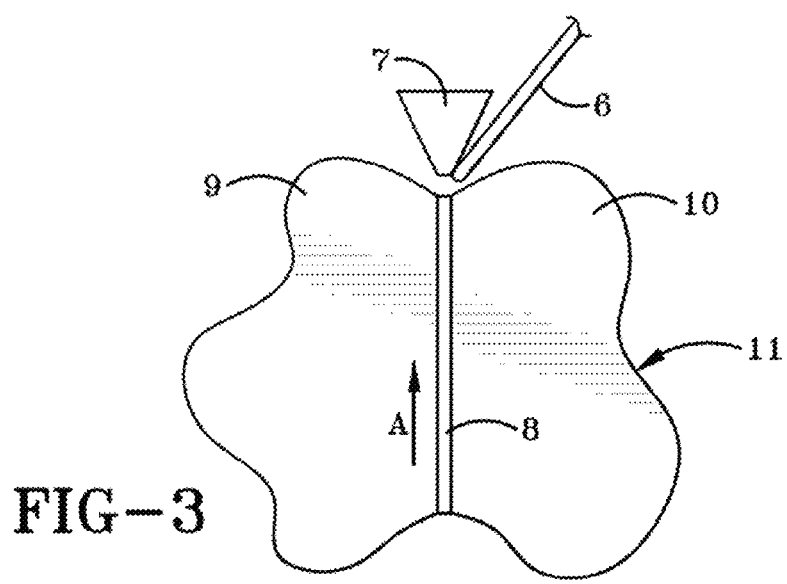
FIG. 3 is a diagrammatic view of a welding machine welding with a trace boron titanium base alloy welding wire used to form a weld which secures two parts together to form an article of the two welded parts.

Referring to FIG. 3, trace boron titanium base alloy welding wire 6 is shown used with a welding machine 7, which may move (Arrow A) to weld with wire 6 to form a weld 8 which secures first and second titanium base alloy parts 9 and 10 together to form an article 11 which includes the two welded parts 9 and 10 and weld 8. Thus, a standard welder or welding machine 7 may form weld 8 from welding wire 6 by melting wire 6 to form molten material which cools and solidifies to form weld 8. The molten material and resulting weld 8 may have essentially the same chemical composition as wire 6 or may have a chemical composition which is a combination of the chemical composition of wire 6 and the chemical composition of the titanium base alloy of which parts 9 and 10 are formed.

Welding wire 6 may be formed of any titanium base alloy which includes boron in an amount of 0.05 to 0.20 weight percent. The amount of boron may be in a range of 0.05 or 0.10 to 0.10, 0.15 or 0.20. Such a trace boron titanium base alloy, may include, for example, CP-Ti-0.05-0.20B, Ti-6Al-4V-0.05-0.20B, Ti-5Al-2Sn-2Zr-4Mo-4Cr-0.05-0.20B, Ti-6Al-2Sn-4Zr-2Mo-0.05-0.20B, Ti-6Al-2Sn-4Zr-2Mo-0.1Si-0.05-0.20B, Ti-10V-2Fe-3Al-0.05-0.20B, Ti-6Al- 2Sn-4Zr-6Mo-0.05-0.20B, Ti-5Al-2.5Sn-0.05-0.20B, Ti-3Al-2.5V-0.05-0.20B, Ti-6Al-4V-0.05-0.20B Extra Low Interstitial, Ti-6Al-6V-2Sn-0.05-0.20B, Ti-15Mo-2.7Nb-3Al-0.2Si-0.05-0.20B, Ti-3Al-8V-6Cr-4Mo-4Zr-0.05-0.20B and Ti-5Al-5V-5Mo-3Cr-0.05-0.20B.

Each of parts 9 and 10 may be formed of any titanium base alloy which may or may not include trace boron in an amount of 0.05 to 0.20 weight percent. Thus, for instance, each of parts 9 and 10 may be formed of one of CP-Ti, Ti-6Al-4V, Ti-5Al-2Sn-2Zr-4Mo-4Cr, Ti-6Al-2Sn-4Zr-2Mo, Ti-6Al-2Sn-4Zr-2Mo-0.1Si, Ti-10V-2Fe-3Al, Ti-6Al-2Sn-4Zr-6Mo, Ti-5Al-2.5Sn, Ti-3Al-2.5V, Ti-6Al-4V Extra Low Interstitial, Ti-6Al-6V-2Sn, Ti-15Mo-2.7Nb-3Al-0.2Si, Ti-3Al-8V-6Cr-4Mo-4Zr, Ti-5Al-5V-5Mo-3Cr, CP-Ti-0.05-0.20B, Ti-6Al-4V-0.05-0.20B, Ti-5Al-2Sn-2Zr-4Mo-4Cr-0.05-0.20B, Ti-6Al-2Sn-4Zr-2Mo-0.05-0.20B, Ti-6Al-2Sn-4Zr-2Mo-0.1Si-0.05-0.20B, Ti-10V-2Fe-3Al-0.05-0.20B, Ti-6Al-2Sn-4Zr-6Mo-0.05-0.20B, Ti-5Al-2.5Sn-0.05-0.20B, Ti-3Al-2.5V-0.05-0.20B, Ti-6Al-4V-0.05-0.20B Extra Low Interstitial, Ti-6Al-6V-2Sn-0.05-0.20B, Ti-15Mo-2.7Nb-3Al-0.2Si-0.05-0.20B, Ti-3Al-8V-6Cr-4Mo-4Zr-0.05-0.20B and Ti-5Al-5V-5Mo-3Cr-0.05-0.20B. Parts 9 and 10 may be formed of the same titanium base alloy or of different titanium base alloys. Each of parts 9 and 10 may also be a titanium base alloy which is the same as or different than the titanium base alloy of which weld 8 is formed.

Figure 4:
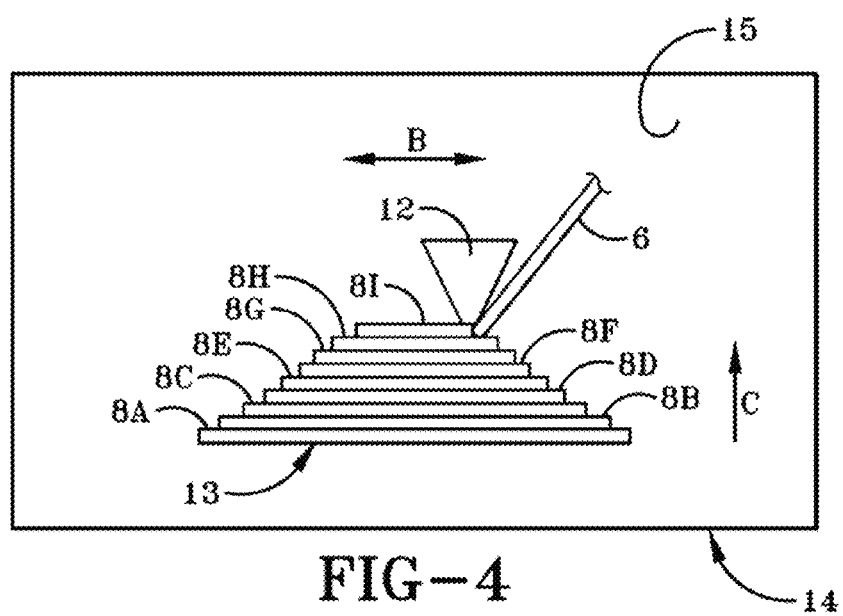
FIG. 4 is a diagrammatic view of an electron beam additive manufacturing machine which has formed a near shape article of superimposed welds layer by layer with a trace boron titanium base alloy welding wire.

Referring now to FIG. 4, trace boron titanium base alloy welding wire 6 is shown used with an electron beam (EB) additive manufacturing machine which includes an electron beam gun 12 which used in welding in a particular manner to form elongated welds or weld layers 8A-8I to form a near shape trace boron titanium base alloy article 13 which includes the welds or weld layers 8A-8I. FIG. 4 also shows a chamber or chamber wall 14 defining an interior chamber 15 in which are disposed the additive manufacturing machine/gun 12, welds 8A-8I and article 13. Interior chamber is under a high vacuum during the additive manufacturing process suitable to the use of electron beam gun 12. Such electron beam additive manufacturing systems are produced and operated by Sciaky Inc. of Chicago, Ill.

Broadly, the additive manufacturing machine is computer controlled (commonly via computer numeric controls or CNC) to sequentially form welds 8A-I in a layer-by-layer manner to build up the resulting article such as article 13. The EB gun is moved along a computer controlled welding path as welding wire moves along with the gun and is continuously fed to a melting point of the gun to produce an elongated weld or weld layer. Thus, the machine first produces weld 8A, for instance while the gun and welding wire are moving in a first direction, and then weld 8B superimposed on weld 8A, for instance while the gun and welding wire are moving in a second opposite direction (although the direction could be the same). In one scenario, the gun moves back and forth (Arrow B), getting higher (Arrow C) with each pass such that the gun lays down a weld with each pass so that each subsequent weld or weld layer is laid down on or welded to the immediately preceding weld or weld layer. In another scenario, gun 12 may move in a looping manner. For instance, gun 12 may move along an essentially circular path while continuously melting wire 6 to produce an essentially circular weld layer, and then continue along sequential essentially circular paths to produce additional essentially circular weld layers respectively superimposed on and secured to the immediately previous layer and/or to other weld layers. Such a scenario may produce an article having a cylindrical shape or a conical shape or other shapes. Similarly, gun 12 may move along repeated oval paths or rectangular paths or square paths or octagonal paths or any kind of polygonal shape paths or other type of paths. As will be understood, article 13 represents only one of a limitless number of configurations of the type of article that may be produced by additive manufacturing. In short, article 13 or any other article formed by this process is typically made up of a plurality of welds or weld layers such as 8A-I which are superimposed on one another, with each weld or weld layer being welded/secured to one or more welds or weld layers.

For use in the EB additive manufacturing process (or other processes), welding wire 6 may be a special chemistry titanium alloy welding wire formulated to meet final chemistry specifications which may differ from the initial chemistry of the welding wire itself. For example, as noted above EB additive manufacturing requires a high vacuum for using the EB gun. Due to this high vacuum, welding wire which includes a certain element (relatively more volatile) such as aluminum is specially configured with a higher weight percentage of the certain element due to the vaporization of the certain element when under high vacuum. Thus, in order to produce welds or weld layers in this situation of a given final alloy composition, the welding wire has an initial composition in which the certain element has an increased percentage. Although the increased amount will vary depending on the specific alloy at issue and other factors, welding wire which includes aluminum may have a weight percentage of aluminum which is, for example, 0.5 to 1.0, 1.5 or 2.0 weight percent more than the desired final composition of the weld or weld layer produced from the welding wire by the additive manufacturing process or other high vacuum process.

Thus, for instance, to produce a weld/weld layer such as 8A-8I in a high vacuum environment such as EB additive manufacturing, in which the weld/weld layer has a composition of Ti-6Al-4V-(0.05-0.2)B, Ti-5Al-2Sn-2Zr-4Mo-4Cr-(0.05-0.2)B, Ti-6Al-2Sn-4Zr-2Mo-(0.05-0.2)B, Ti-6Al-2Sn-4Zr-2Mo-0.1Si-(0.05-0.2)B, Ti-10V-2Fe-3Al-(0.05-0.2)B, Ti-6Al-2Sn-4Zr-6Mo-(0.05-0.2)B, Ti-5Al-2.5Sn-(0.05-0.2)B, Ti-3Al-2.5V-(0.05-0.2)B, Ti-6Al-4V-(0.05-0.2)B extra low interstitial, Ti-6Al-6V-2Sn-(0.05-0.2)B, Ti-15Mo-2.7Nb-3Al-0.2Si-(0.05-0.2)B, Ti-3Al-8V-6Cr-4Mo-4Zr-(0.05-0.2)B or Ti-5Al-5V-5Mo-3Cr-(0.05-0.2)B, the welding wire may respectively have an initial composition of Ti-(6.5-8)Al-4V-(0.05-0.2)B, Ti-(5.5-7)Al-2Sn-2Zr-4Mo-4Cr-(0.05-0.2)B, Ti-(6.5-8)Al-2Sn-4Zr-2Mo-(0.05-0.2)B, Ti-(6.5-8)Al-2Sn-4Zr-2Mo-0.1Si-(0.05-0.2)B, Ti-10V-2Fe-(3.5-5)Al-(0.05-0.2)B, Ti-(6.5-8)Al-2Sn-4Zr-6Mo-(0.05-0.2)B, Ti-(5.5-7)Al-2.5Sn-(0.05-0.2)B, Ti-(3.5-5)Al-2.5V-(0.05-0.2)B, Ti-(6.5-8)Al-4V-(0.05-0.2)B extra low interstitial, Ti-(6.5-8)Al-6V-2Sn-(0.05-0.2)B, Ti-15Mo-2.7Nb-(3.5-5)Al-0.2Si-(0.05-0.2)B, Ti-(3.5-5)Al-8V-6Cr-4Mo-4Zr-(0.05-0.2)B or Ti-(5.5-7)Al-5V-5Mo-3Cr-(0.05-0.2)B.

A standard welder and an EB gun are noted above for use in forming the various welds 8 from welding wire 6. It will be understood that any suitable heat source known in the art and any suitable welding machine capable of utilizing welding wire 6 may be used to produce welds from wire 6, whether in a standard atmosphere such as at a standard ambient atmospheric temperature and pressure in air, in a high or low vacuum atmosphere, in an inert gas atmosphere and so forth.

Figure 5:
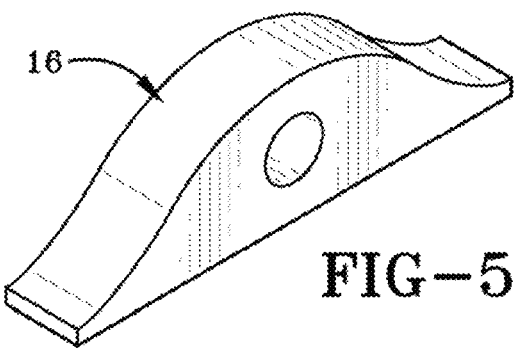
FIG. 5 is a perspective view of a final shape article derived from the near shape article of FIG. 4.

FIG. 5 shows a final shape article 16 derived from near shape article 13. Article 13 may be machined by any suitable method to produce article 16. For instance, such machining may be under control of a computer, such as a CNC device.

In the case shown, article 13 has been machined to remove the ends and edges of welds 8A-8I to provide the upper curved surface and flat vertical side surfaces of article 16, which is also shown with a hole formed therein.

Figure 6:
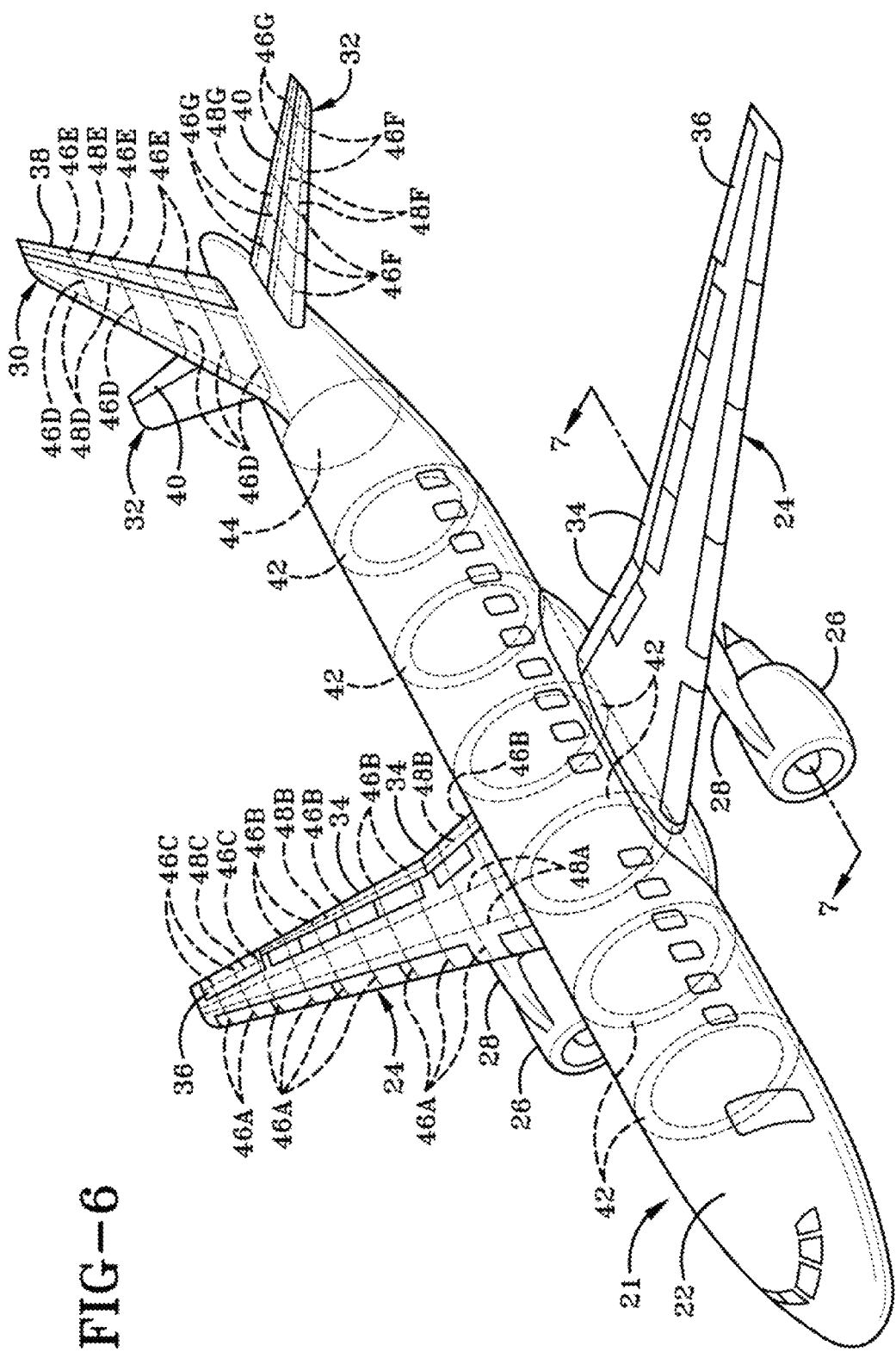
FIG. 6 is a diagrammatic view of an aircraft showing various aircraft structural components which may be formed by additive manufacturing using the trace boron titanium base alloy welding wire.
Figure 7:
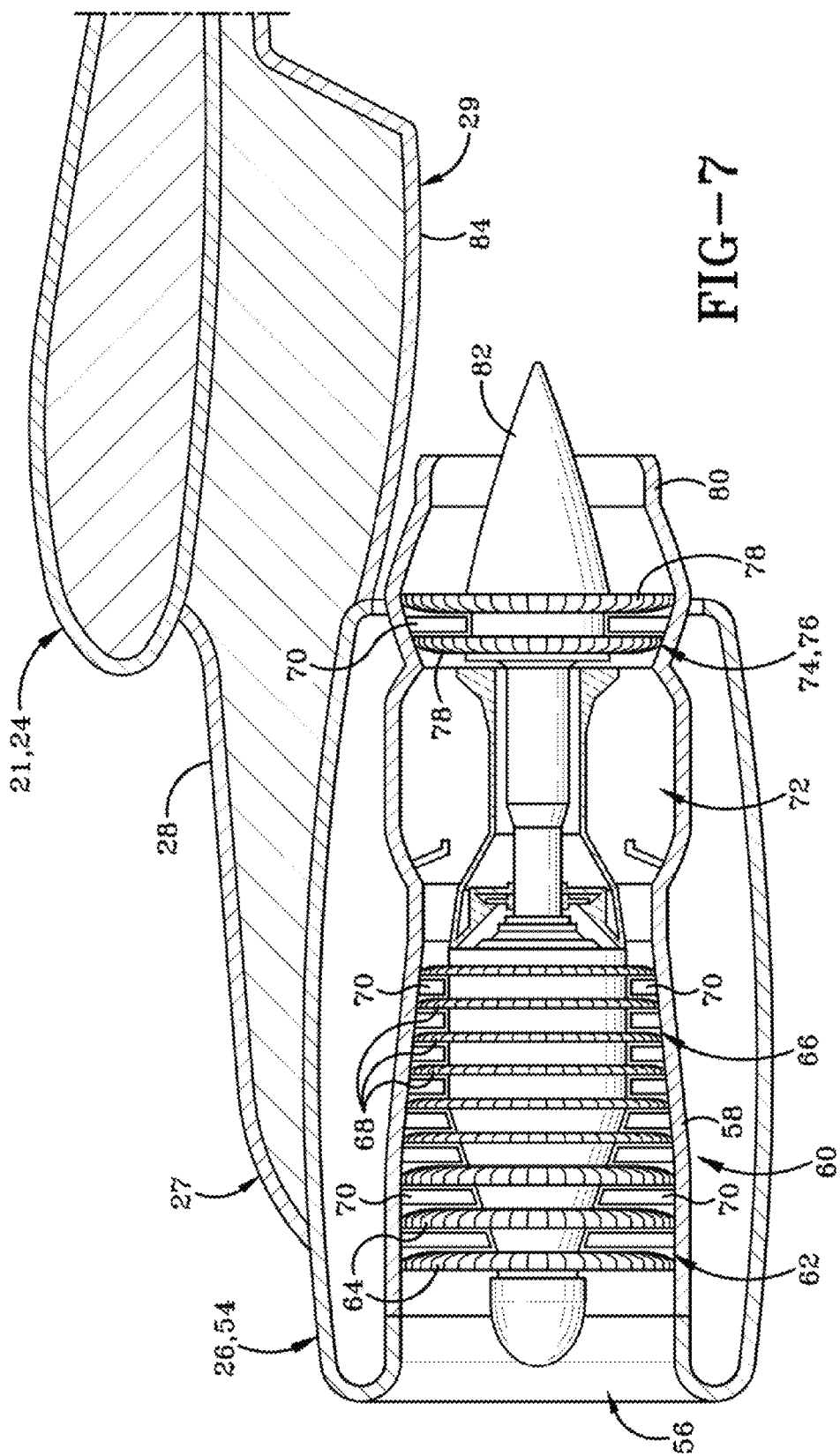
FIG. 7 is a sectional view taken on line 7-7 of FIG. 6 showing various aircraft engine components which may be formed by additive manufacturing using the trace boron titanium base alloy welding wire.

As noted above, a limitless number of shapes may be formed by additive manufacturing. FIGS. 6-7 are provided to illustrate some of the components which may be formed using the trace boron titanium base alloy welds or weld layers (such as 8A-I) of the additive manufacturing process from trace boron titanium base alloy welding wire 6. These and other components may be formed entirely of such welds or weld layers, or a portion of such components may be formed of such welds or weld layers.

Referring to FIG. 6, an aircraft 21 is shown having a fuselage 22, left and right wings 24 and gas turbine engines 26 mounted on aircraft wings 24 via respective pylons 28. Aircraft 21 further includes a tail assembly or empennage comprising a vertical stabilizer 30 and left and right horizontal stabilizers 32. Flaps 34 and ailerons 36 are respectively mounted on wings 24. A rudder 38 is mounted on vertical stabilizer 30, and elevators 40 are mounted respectively on horizontal stabilizers 32. Fuselage 2 comprises a plurality of annular formers 42 to which the skin of the fuselage is attached and a bulkhead 44 adjacent the empennage. Bulkhead 44 is an example of various types of bulkheads which may be located at various locations in the aircraft. Aircraft 21 includes multiple ribs 46 and spars 48. For example, ribs 46 may include wing ribs 46A, flap ribs 46B, aileron ribs 46C, vertical stabilizer ribs 46D, rudder ribs 46E, horizontal stabilizer ribs 46F and elevator ribs 46G. Spars 48 may, for example, include wing spars 48A, flap spars 48B, aileron spars 48C, vertical stabilizer spars 48D, rudder spars 48E, horizontal stabilizer spars 48F and elevator spars 48G.

FIG. 7 shows that in the sample aircraft 21, pylon 28 is secured to wing 24 and extends downwardly and forward therefrom with aircraft engine 26 secured to and extending downwardly from pylon 28. More particularly, pylon 28 has a forward section 27 and a rear or aft section 29 such that the top of rear section 29 is secured to the bottom of wing 24 and the bottom of front section 27 is secured to the top of engine 26. Engine 26 may include a nacelle 54 with a front end defining an air intake 56, an engine casing 58, a compressor section 60 which may include a low pressure compressor 62 with low pressure rotary compressor blades 64 and a high pressure compressor 66 with high pressure rotary compressor blades 68, static or stator airfoils or vanes 70, a combustion chamber 72, a turbine section 74 which may include a turbine 76 with rotary turbine blades 78, an exhaust system including an exhaust nozzle or nozzle assembly 80 and an exhaust plug 82. Vanes 70 may be in compressor section 60 and/or turbine section 74. Aft pylon 28 includes various aft pylon components including a heat shield 84 along the bottom of pylon 28. One heat shield representative of the type of heat shield shown at 84 is disclosed in U.S. Pat. No. 7,943,227, which is incorporated herein by reference. Another such heat shield, also referred to as an aft pylon fairing, is disclosed in US Patent Application Publication 2011/0155847, which is also incorporated herein by reference.

Additive manufacturing may be used to form articles such as aircraft components from wire 6, including both aircraft engine components and non-engine components. Although not an exhaustive list, such aircraft components may include formers such as formers 42, bulkheads such as bulkhead 44, ribs such as ribs 46, spars such as spars 48, pylons such as pylon 28, nacelles such as nacelle 54, engine casings such as casing 58, vanes such as vanes 70, exhaust nozzles such as nozzle 80, exhaust plugs such as exhaust plug 82, and heat shields such as heat shield 84. Aircraft components and other types of components may also be formed using wire 6 by the welding of parts together such as discussed above with respect to titanium base alloy parts 9 and 11 whereby such components thus include parts 9 and 11 and weld 8.

Figure 8:
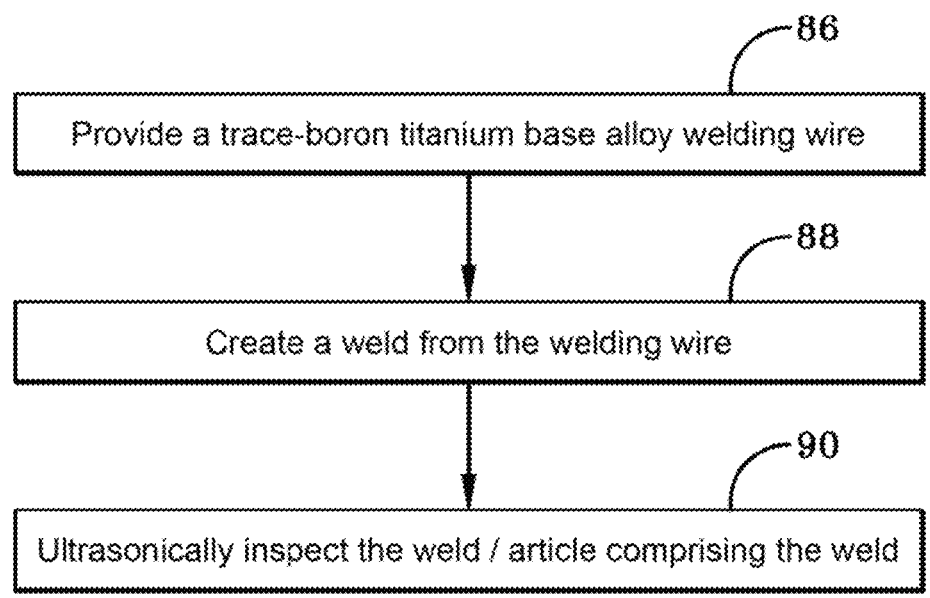
FIG. 8 is a flow chart of a sample method.

FIG. 8 shows a basic method which may include the steps of providing a trace boron titanium base alloy welding wire 6 (block 86), creating one or more welds (such as welds 8) from the welding wire (block 88), and ultrasonically inspecting the one or more welds to determine whether the one or more welds has internal flaws (block 90). The weld or welds may be formed as discussed in greater detail above. The ultrasonic inspection (block 90) may include ultrasonically inspecting an article or component which includes the weld or welds or an article or component which is made essentially entirely from the weld or welds. The ultrasonic inspection may also include ultrasonically inspecting an article or component which includes the weld or welds and titanium base alloy parts secured to one another by the weld or welds, whereby the weld or welds and the parts are ultrasonically inspected. One method may include some or all of the steps shown in FIGS. 2 and 8.

Thus, for instance, an as-cast trace-boron titanium alloy article may be ultrasonically inspected and shipped to a customer before any hot working, such as forging, rolling or extrusion. The customer may then undertake such hot working and may also undertake welding using one or more of such as-cast articles and weld wire 6 to form another article or component which includes parts formed from the as-cast articles and one or more welds formed from wire 6 and joining the parts. The weld(s) or article or component comprising the weld(s) may then be ultrasonically inspected and installed, such as on an aircraft or other product.

In the foregoing description, certain terms have been used for brevity, clearness, and understanding. No unnecessary limitations are to be implied therefrom beyond the requirement of the prior art because such terms are used for descriptive purposes and are intended to be broadly construed.

Moreover, the description and illustration of the invention is an example and the invention is not limited to the exact details shown or described.

The invention claimed is:

1. A method comprising the steps of:
   providing welding wire formed of a titanium base alloy and boron in a range of about 0.05 to 0.20 percent by weight;
   providing first and second titanium base alloy parts; and
   forming at least one weld from the welding wire between the first and second parts to secure the parts to one another.

2. A method comprising the steps of:
   providing welding wire formed of a titanium base alloy and boron in a range of about 0.05 to 0.20 percent by weight;
   forming a first weld layer from the welding wire; and
   forming a second weld layer superimposed on and secured to the first weld layer.

3. A method comprising the steps of:
   providing welding wire formed of a titanium base alloy and boron in a range of about 0.05 to 0.20 percent by weight;
   forming at least one weld from the welding wire; and
   ultrasonically inspecting the at least one weld to determine whether the at least one weld has internal flaws.

4. The method of claim 3 wherein the boron is in a range of about 0.05 to 0.15 percent by weight.

5. The method of claim 4 wherein the boron is in a range of about 0.05 to 0.10 percent by weight.

6. The method of claim 3 wherein the boron is in a range of about 0.10 to 0.20 percent by weight.

7. The method of claim 6 wherein the boron is in a range of about 0.10 to 0.15 percent by weight.

8. The method of claim 3 wherein the titanium base alloy is one of: Ti-6Al-4V, Ti-5Al-2Sn-2Zr-4Mo-4Cr, Ti-6Al-2Sn-4Zr-2Mo, Ti-6Al-2Sn-4Zr-2Mo-0.1 Si, Ti-10V-2Fe-3Al, Ti-6Al-2Sn-4Zr-6Mo, Ti-5Al-2.5Sn, Ti-3Al-2.5V, Ti-6Al-4V extra low interstitial, Ti-6Al-6V-2Sn, Ti-15Mo-2.7Nb-3Al-0.2Si, Ti-3Al-8V-6Cr-4Mo-4Zr and Ti-5Al-5V-5Mo-3Cr.

9. The method of claim 3 wherein the titanium base alloy is one of: Ti-(6.5-8)Al-4V, Ti-(5.5-7)Al-2Sn-2Zr-4Mo-4Cr, Ti-(6.5-8)Al-2Sn-4Zr-2Mo, Ti-(6.5-8)Al-2Sn-4Zr-2Mo-0.1 Si, Ti-10V-2Fe-(3.5-5)Al, Ti-(6.5-8)Al-2Sn-4Zr-6Mo, Ti-(5.5-7)Al-2.5Sn, Ti-(3.5-5)Al-2.5V, Ti-(6.5-8)Al-4V extra low interstitial, Ti-(6.5-8)Al-6V-2Sn, Ti-15Mo-2.7Nb-(3.5-5)Al-0.2Si, Ti-(3.5-5)Al-8V-6Cr-4Mo-4Zr or Ti-(5.5-7)Al-5V-5Mo-3Cr.

10. The method of claim 3 wherein the at least one weld comprises a first weld layer and a second weld layer superimposed on and secured to the first weld layer.

11. The method of claim 10 wherein the at least one weld comprises a third weld layer superimposed on and secured to the second weld layer.

12. The method of claim 3 wherein the at least one weld is applied to an aircraft component.

13. The method of claim 12 wherein the aircraft component is one of a former, a bulkhead, a rib, a spar, a pylon, a nacelle, an engine casing, a vane, an exhaust nozzle, an exhaust plug and a heat shield.

* * * * *